United States Patent
Hirayama et al.

(10) Patent No.: US 9,630,024 B2
(45) Date of Patent: Apr. 25, 2017

(54) RADIATION TREATMENT PLANNING SYSTEM AND METHOD OF RADIATION TREATMENT PLANNING

(71) Applicant: HITACHI, LTD., Tokyo (JP)

(72) Inventors: Shusuke Hirayama, Tokyo (JP); Rintaro Fujimoto, Tokyo (JP)

(73) Assignee: Hitachi, Ltd., Tokyo (JP)

(*) Notice: Subject to any disclaimer, the term of this patent is extended or adjusted under 35 U.S.C. 154(b) by 338 days.

(21) Appl. No.: 14/109,584

(22) Filed: Dec. 17, 2013

(65) Prior Publication Data

US 2014/0206923 A1    Jul. 24, 2014

(30) Foreign Application Priority Data

Jan. 23, 2013    (JP) .................. 2013-009741

(51) Int. Cl.
    *A61N 5/10*    (2006.01)
(52) U.S. Cl.
    CPC .................. *A61N 5/1031* (2013.01)
(58) Field of Classification Search
    CPC .... A61N 5/103; A61N 5/1031; A61N 5/1038; A61N 5/1042; A61N 5/1043; A61N 5/1077
    See application file for complete search history.

(56) References Cited

U.S. PATENT DOCUMENTS

2012/0001085 A1*   1/2012   Fujimoto .............. A61N 5/103
                                              250/396 ML

FOREIGN PATENT DOCUMENTS

WO    2011/162021 A1    12/2011

OTHER PUBLICATIONS

A. Lomax, in "Intensity modulation methods for proton radiotherapy," Phys. Med. Biol. 44 (1999), 185-205.
A. Lomax, in "Intensity modulated proton therapy and its sensitivity to treatment uncertainties 1: the potential effects of calculation uncertainties," Phys. Med. Biol. 53 (2008), 1027-1042.
A. Lomax, in "Intensity modulated proton therapy and its sensitivity to treatment uncertainties 2: the potential effects of inter-fraction and inter-field motions," Phys. Med. Biol. 53 (2008), 1043-1056.

(Continued)

*Primary Examiner* — Charles A Marmor, II
*Assistant Examiner* — Carrie R Dorna
(74) *Attorney, Agent, or Firm* — Mattingly & Malur, PC (57) ABSTRACT

There is disclosed a radiation treatment planning system for preparing treatment planning information for carrying out radiation treatment. The apparatus includes an input unit with which an operator inputs a prescription dose and an irradiation angle; an arithmetic unit which prepares the treatment planning information by determining irradiation conditions in such a manner as to bring a dose distribution calculated based on the result of the input from the input unit closer to the prescription dose, and a display unit which displays the treatment planning information. The arithmetic unit sets, per point for radiation irradiation, an index representing the degree of demand for irradiation amount suppression, the degree of demand determined by the radiation irradiation point, and the arithmetic unit further determines the irradiation conditions using the index.

6 Claims, 10 Drawing Sheets

(56) References Cited

OTHER PUBLICATIONS

J. Unkelbach et al., in "Accounting for range uncertainties in the optimization of intensity modulated proton therapy," Phys. Med. Biol. 52 (2007), 2755-2773.
D. Pflugfelder et al., in "Worst case optimization: a method to account for uncertainties in the optimization of intensity modulated proton therapy," Phys. Med. Biol. 53 (2008), 1689-1700.
Japanese Office Action received in corresponding Japanese Application No. 2013-009741 dated Jan. 26, 2016.

* cited by examiner

RADIATION TREATMENT PLANNING SYSTEM AND METHOD OF RADIATION TREATMENT PLANNING

BACKGROUND OF THE INVENTION

1. Field of the Invention

The present invention relates to a radiation treatment planning system and a method of radiation treatment planning.

2. Description of the Related Art

Radiation treatment involves irradiating the tumor cells constituting the target with radiation for treatment. Whereas X-rays are the most commonly employed radiation in radiation treatment, demand has been growing for treatments that use particle beams (charged particle beams) typified by proton beam and carbon ion beam offering high dose concentration on the target.

In radiation treatment, excessive or insufficient doses of irradiation can lead to adverse effects on normal tissues other than the tumor or a relapse of the tumor. It is thus required that the tumor region be irradiated with a dose as accurate as possible and as concentrated as possible.

An X-ray-based therapy called IMRT (Intensity Modulated Radiation Therapy) involves giving irradiation in multiple directions while varying the collimator shape. Where the target region of a complicated shape is irradiated, this therapy can minimize the dose with which the surrounding normal tissues are irradiated. In the treatment using particle beams, numerous fine beams with their intensities modulated are applied at a plurality of irradiation angles, which is known as IMPT (Intensity Modulated Proton Therapy) whereby a uniform dose distribution is provided over the target region.

IMPT is implemented using the scanning irradiation method. The scanning irradiation method involves causing a pair of scanning magnets to deflect fine charged particle beams to a desired point on a plane. The method allows the inside of the tumor to be irradiated in a filling manner so that a high dose is applied only to the tumor region. With this method, diverse dose distributions can be formed easily.

With IMRT and IMPT, what is very important is the process of preparing the treatment plan using a radiation treatment planning system before actual irradiation. The radiation treatment planning system simulates by numerical calculation the dose distribution inside the patient's body based on the information about the inside of the patient's body obtained from computed tomography images or the like. The operator of the radiation treatment planning system determines irradiation conditions such as the direction and energy in which radiation is applied, the irradiation point and the irradiation amount, by referring to the results of the calculations performed by the apparatus. The generally practiced process in this regard is outlined below.

First, the operator inputs the target region to be irradiated with radiation. What is input here is the region targeted to be sliced into images mainly using CT images. When the operator registers the input data with the radiation treatment planning system, the data is stored as three-dimensional region data into a memory of the radiation treatment planning system. If necessary, the operator may also input and register the position of organ at risk.

The operator then sets the prescription doses constituting the target doses for the registered regions. The settings are made for the target region and the organ at risk, which are registered earlier. With regard to the target region, for example, a dose sufficient for necrotizing the tumor is designated. In many cases, a minimum value and a maximum value of the dose with which to irradiate are designated for the target region. On the other hand, a maximum permissible dose is designated regarding the organ at risk.

It is the radiation treatment planning system that determines the beam irradiation point and irradiation amount for implementing the dose distribution designated by the operator. Usually, the irradiation point is determined first. Thereafter, the irradiation amount is determined in a manner that meets the dose distribution conditions input by the operator.

A widely adopted method for efficiently determining the irradiation amount involves using an objective function that quantities the divergence from the prescription dose, as described by A. Lomax, in "Intensity modulation methods for proton radiotherapy," Phys. Med. Biol. 44 (1999), 185-205 (Non-Patent Literature 1). The objective function is defined to be smaller the more closely the dose distribution meets the prescription dose. A search is made for an irradiation amount that minimizes the objective function through iterative calculation, whereby an optimum irradiation amount is calculated.

As a result, it is possible to calculate the irradiation amount for obtaining the dose distribution that satisfies the prescription dose. However, there exist numerous uncertainties such as those in setup the patient (setup error), in letting the target be moved by respiration (respiratory movement error), and in converting CT values to water equivalent thickness (range error), as described by A. Lomax, in "Intensity modulated proton therapy and its sensitivity to treatment uncertainties 1: the potential effects of calculation uncertainties," Phys. Med. Biol. 53 (2008), 1027-1042 (Non-Patent Literature 2) and also by A. Lomax, in "Intensity modulated proton therapy and its sensitivity to treatment uncertainties 2: the potential effects of inter-fraction and inter-field motions," Phys. Med. Biol. 53 (2008), 1043-1056 (Non-Patent Literature 3).

Given the above-mentioned uncertainties, there is a possibility that the dose distribution inside the patient's body under irradiation may not match the dose distribution of the prepared treatment plan. Particularly with IMRT and IMPT, the effects of these uncertainties can become prominent because a desired dose distribution is formed by preparing and adding up uneven dose distributions applied in a plurality of irradiation directions.

In order to alleviate the effects of such uncertainties upon preparation of a treatment plan, there have been proposed several techniques that focus attention on characteristics other than the divergence between the dose of each region (target region and organ at risk) and the prescription dose. For example, according to one technique, on the assumption that the range of the beam applied to the target is varied randomly, optimized calculation is performed of the values of the dose provided by the beam and of the objective function so as to lower the sensitivity of the dose distribution in the face of range uncertainties, as described by J. Unkelbach et al., in "Accounting for range uncertainties in the optimization of intensity modulated proton therapy," Phys. Med. Biol. 52 (2007), 2755-2773 (Non-Patent Literature 4). According to another technique, as described by D. Pflugfelder et al., in "Worst case optimization: a method to account for uncertainties in the optimization of intensity modulated proton therapy," Phys. Med. Biol. 53 (2008), 1689-1700 (Non-Patent Literature 5), the dose distribution in effect when a setup error has occurred in addition to the range error is calculated under a plurality of conditions. Information about a maximum divergence between the calculated dose of each region and the prescription dose is added to the objective function as another item for optimized calculation. When the range error and setup error take place, this technique makes it possible to reduce the maximum divergence between the dose of each region and the prescription dose and thereby lower the sensitivity of the dose distribution in the face of range and setup uncertainties.

SUMMARY OF THE INVENTION

Meanwhile, the sensitivity of the treatment plan to uncertainties can also be reduced by suppressing the irradiation to the regions that have been determined by experience to be highly vulnerable to uncertainties. For example, if the operator determines that the range error is pronounced in a metal artifact portion, in the vicinity of bones, or in other regions where density varies greatly, a treatment plan that suppresses irradiation to these regions need only be prepared.

In this regard, simply suppressing the irradiation amount to a given region can result in a dose distribution that diverges significantly from the prescription dose. Thus it is necessary for the radiation treatment planning system to minimize the irradiation amount to a particular region while bringing the dose distribution closer to the prescription dose. However, whereas related-art radiation treatment planning systems have been capable of exercising control to bring the dose distribution closer to the target distribution, there has yet to be a radiation treatment planning system offering the function of directly controlling the irradiation amount to a specific region during optimized calculation.

In solving the foregoing and other problems of the related art and according to one aspect of the invention, there is provided a radiation treatment planning system for preparing treatment planning information for carrying out radiation treatment, the radiation treatment planning system including: an input unit with which an operator inputs a prescription dose and an irradiation angle; an arithmetic unit which prepares the treatment planning information by determining irradiation conditions in such a manner as to bring a dose distribution calculated based on the result of the input from the input unit closer to the prescription dose, and a display unit which displays the treatment planning information. The arithmetic unit sets, per point for radiation irradiation, an index representing the degree of demand for irradiation amount suppression, which is determined by the radiation irradiation point. The arithmetic unit further determines the irradiation conditions using the index.

According to the present invention, it is possible to prepare the irradiation conditions that suppress the worsening of the dose distribution in the patient's body attributable to uncertainties in preparing the treatment plan.

BRIEF DESCRIPTION OF THE DRAWINGS

Further objects and advantages of the present disclosure will become apparent upon a reading of the following description and appended drawings in which.

DESCRIPTION OF THE PREFERRED EMBODIMENTS

Some embodiments of the radiation treatment planning system and treatment planning method according to the present invention are explained hereunder with reference to the accompanying drawings.

A radiation treatment planning system 301 as one embodiment of this invention is explained with reference to FIGS. 1 through 3. Although the treatment planning system 301 of this embodiment will be explained on the assumption that treatment plans using the scanning irradiation method are prepared for particle therapy, the apparatus can also be adapted to cases where treatment plans of radiation treatment using other kinds of radiation such as X-rays and gamma rays are prepared.

Figure 1:
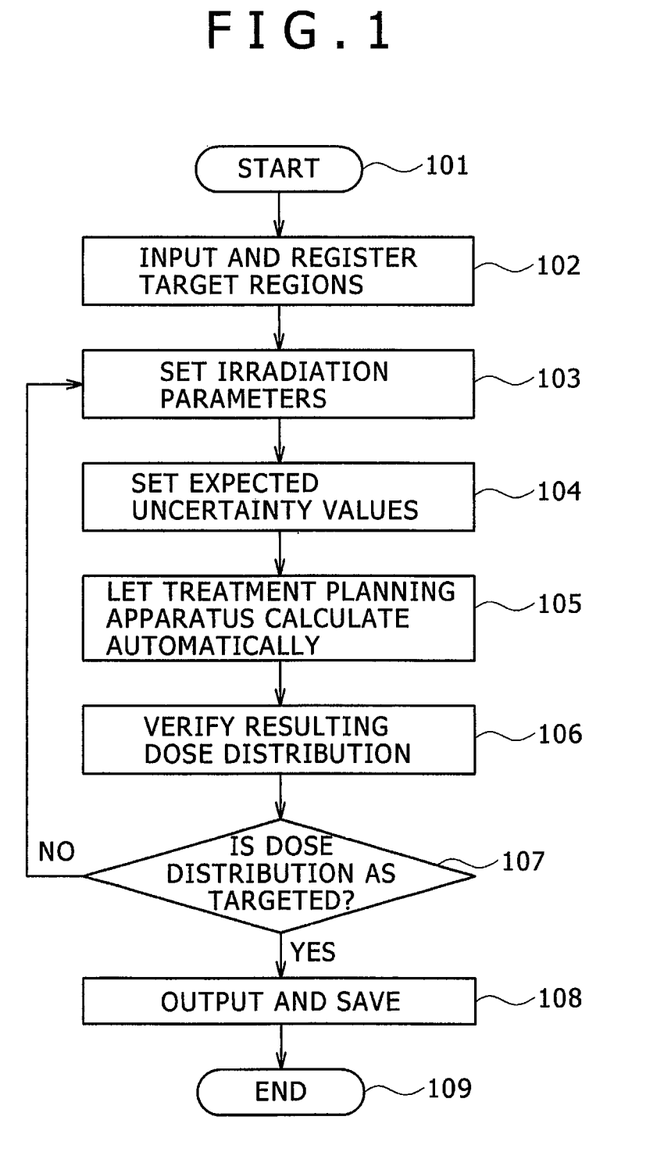
FIG. 1 is a flowchart showing the flow in which a treatment plan is prepared by one preferred, embodiment of the present invention.
Figure 2:
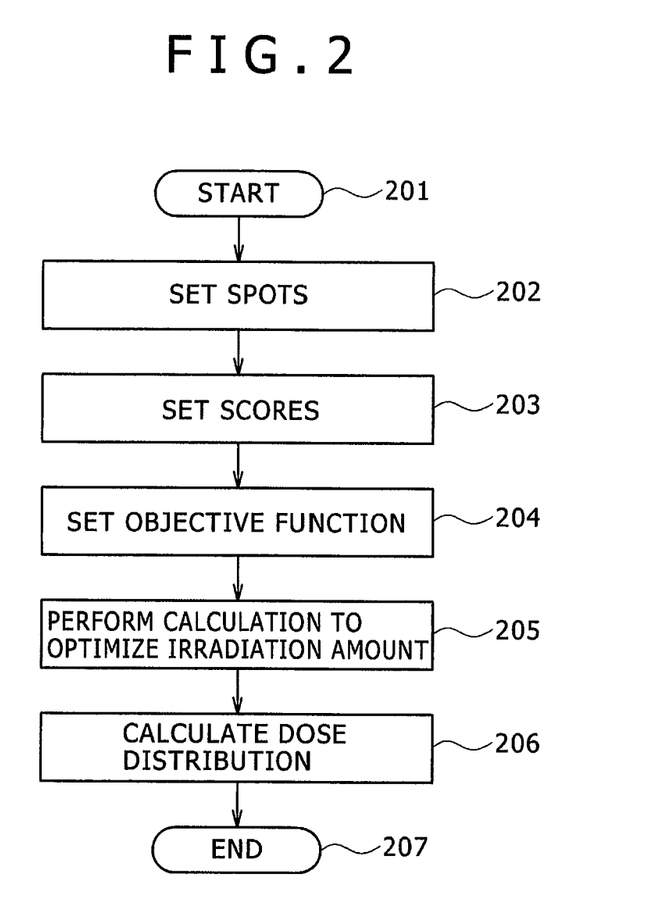
FIG. 2 is a flowchart showing the flow of processing performed by an apparatus as one preferred embodiment of the present invention.

FIG. 1 is a flowchart showing the flow in which a treatment plan is prepared using the radiation treatment planning system (called the treatment planning system hereunder) 301 of this embodiment. FIG. 2 is a flowchart showing the flow of processing performed by the treatment planning system 301 of this embodiment. FIG. 2 details step 105 in FIG. 5 (i.e., step of automatic calculation by the treatment planning system). FIG. 3 shows an overall structure of the treatment planning system 301.

Figure 3:
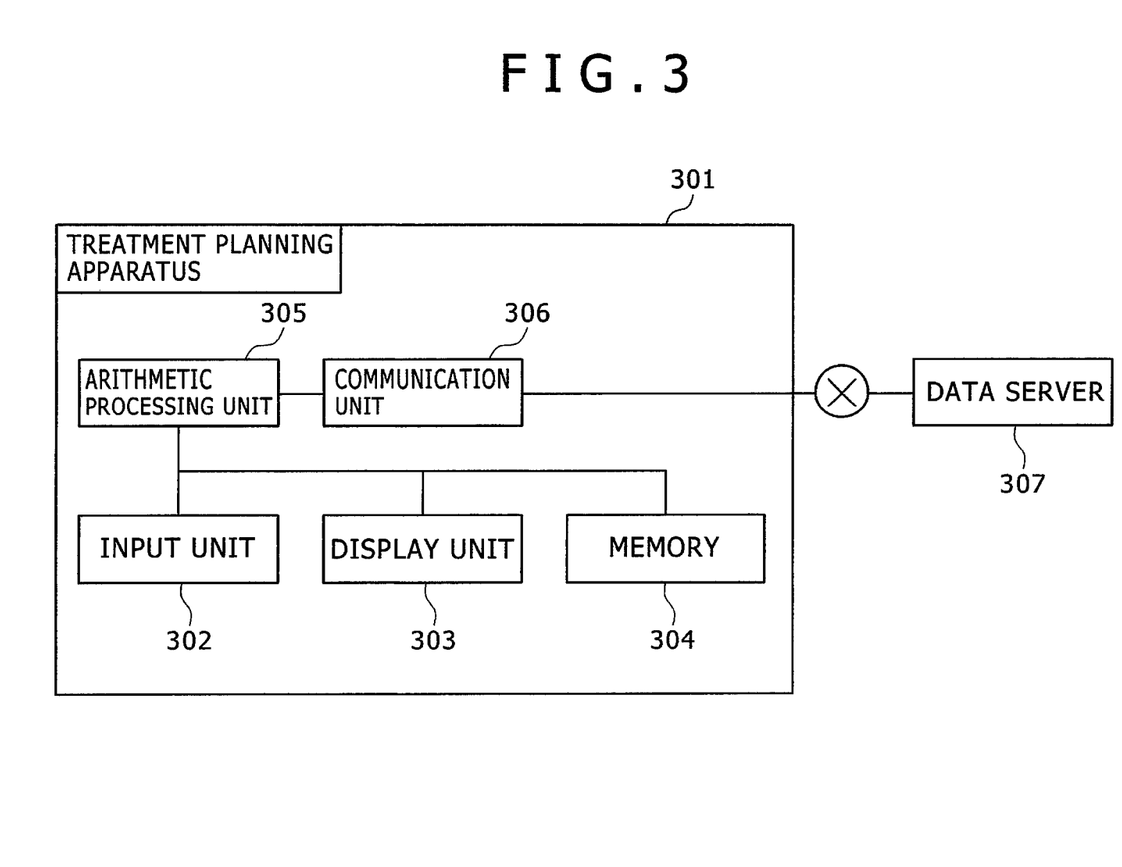
FIG. 3 is an explanatory view showing the structure of a treatment planning system as one preferred embodiment of the present invention.

As shown in FIG. 3, the treatment planning system 301 includes an input unit 302, a display unit 303, a memory 304, an arithmetic processing unit 305, and a communication unit 306. The arithmetic processing unit 305 is connected to the input unit 302, display unit 303, memory (storage unit) 304, and communication unit 306. The treatment planning system 301 is connected to a data server 307 via a network. Specifically, the communication unit 306 of the treatment planning system 301 is connected to the data server 307 via the network and exchanges data with the server.

It is assumed that the patient to be treatment has had treatment planning of computed tomography images obtained beforehand using a CT apparatus. The data about the treatment planning of computed tomography images acquired by the CT apparatus (CT data) is stored in the data server 307. The CT data is three-dimensional data made of CT values recorded per small region called a voxel. The treatment planning system 301 uses the CT data in preparing the treatment plan.

When a healthcare professional (engineer or physician) acting as the operator inputs patient information (patient ID) through the input unit 302, the treatment planning system 301 starts to prepare treatment planning information about the patient corresponding to the patient ID (step 101). First, the input unit 302 outputs the input patient ID to the arithmetic processing unit 305. Based on the input patient ID, the arithmetic processing unit 305 reads the CT data about the target patient from the data server 307. That is, the treatment planning system 301 receives the CT data about the patient corresponding to the patient ID from the data server 307 via the network connected to the communication unit 306, and stores the received CT data into the memory 304. Also, the treatment planning system 301 prepares a computed tomography image for the treatment plan based on the received CT data and causes the display unit 303 to display the prepared computed tomography image. The display unit 303 displays the image in slices (layers) dividing the region including the patient's target volume.

Figure 4:
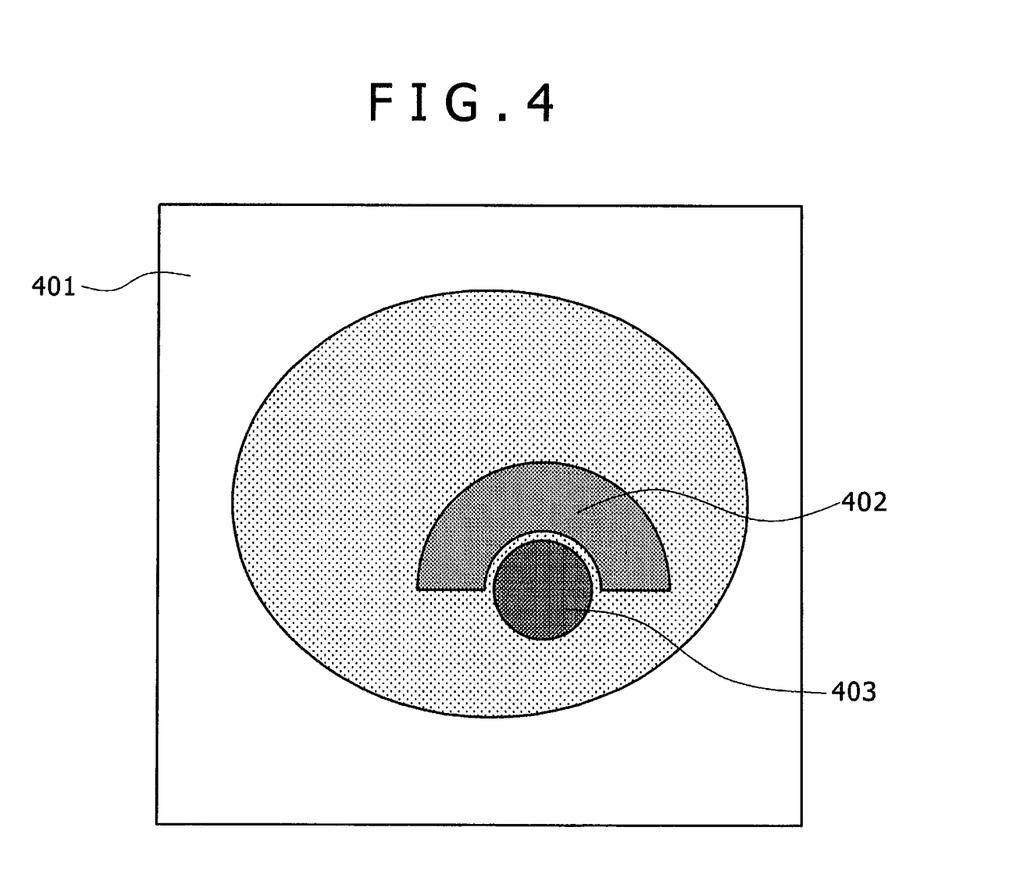
FIG. 4 is a schematic view for explaining how a target region and an organ at risk are input in a slice of CT data.

The operator inputs the region to be designated as the target (target region) per slice of the CT image, using the input unit 302 (a mouse or the like) while verifying the computed tomography image displayed on the display unit 303. The target region is a region that includes an area determined by the operator to be the patient's tumor region that should be irradiated with a particle beam. Upon completion of the input of the target regions into all slices, the operator inputs an input end signal through the input unit 302. Upon receipt of the input end signal, the treatment planning system 301 stores the information about the target regions in all slices into the memory 304 for registration (step 103). The information registered in the memory 304 is three-dimensional information indicative of the target regions input by the operator. If there exists, near the target region, an organ at risk to which the irradiation amount should be minimized or if there is a region that needs to be evaluated or otherwise controlled, the operator inputs through the input unit 302 the position information about the organ at risk and other related parts based on the image information displayed on the display unit 303. As with the information about the target regions, the position information about the organ at risk and other related parts is stored into the memory 304 for registration. FIG. 4 shows a typical display on the display unit 303 indicating an input target region 402 and an input region 403 of an organ at risk or the like in a given slice (layer) 401 generated from the CT data and covering the target volume.

Next, the operator designates the direction of irradiation. If irradiation is to be performed in a plurality of directions, a plurality of angles are to be selected. Other parameters to be determined by the operator for irradiation include dose values (prescription doses) to be applied to the regions registered in step 102 and the spacing between adjacent spots. The prescription doses include the target dose to be applied to the target and a maximum dose that needs to be avoided by the organ at risk. An initial value of the spot-to-spot spacing in the lateral direction is automatically determined to be approximately the same as the beam size of a charged particle beam. Alternatively, the spacing can be changed by the operator. The operator sets such necessary irradiation parameters (step 103).

After setting the necessary irradiation parameters, the operator sets expected values of uncertainties in preparing the treatment plan (step 104). Using the input unit 302, the operator inputs the expected uncertainty values in millimeters (mm) or in percentage points (%).

With the expected uncertainty vales thus set, the treatment planning system 301 performs automatic calculation (step 201). First, the arithmetic processing unit 305 starts to select the points of irradiation from the CT data read into the memory 304 and from the region information input by the operator (step 202). How spot locations (to be explained below) are to be selected is explained below with reference to FIG. 5. At the time of irradiation, the center of gravity of the target region 402 is expected to coincide with an isocenter (rotation center location of a rotating irradiation system (not shown) in the particle therapy apparatus) 501. The irradiation points are defined on the coordinates of a plane (isocenter plane) 504 perpendicular to a straight line 503 including the isocenter 501 and connecting a scan center point (radiation source) 502 with the isocenter 501. In the ensuing description, the plane 504 will be referred to as the isocenter plane and the straight line 503 as the beam central axis. For example, suppose that a point 505 on the isocenter plane 504 is selected as the irradiation point. The treatment planning system 301 searches for an energy level (or levels) that will make the beam stop approximately within the target when the beam is emitted along a straight line 506 connecting the radiation source 502 with the point 505, and selects the energy level (or levels) thus searched for as the energy to be applied to the location of the point 505. This process is performed on all irradiation points set on the isocenter plane 504, which determines pairs of the irradiation point on the isocenter plane 504 and the corresponding energy necessary for the target to be irradiated (the pairs are called the spots hereunder).

Figure 5:
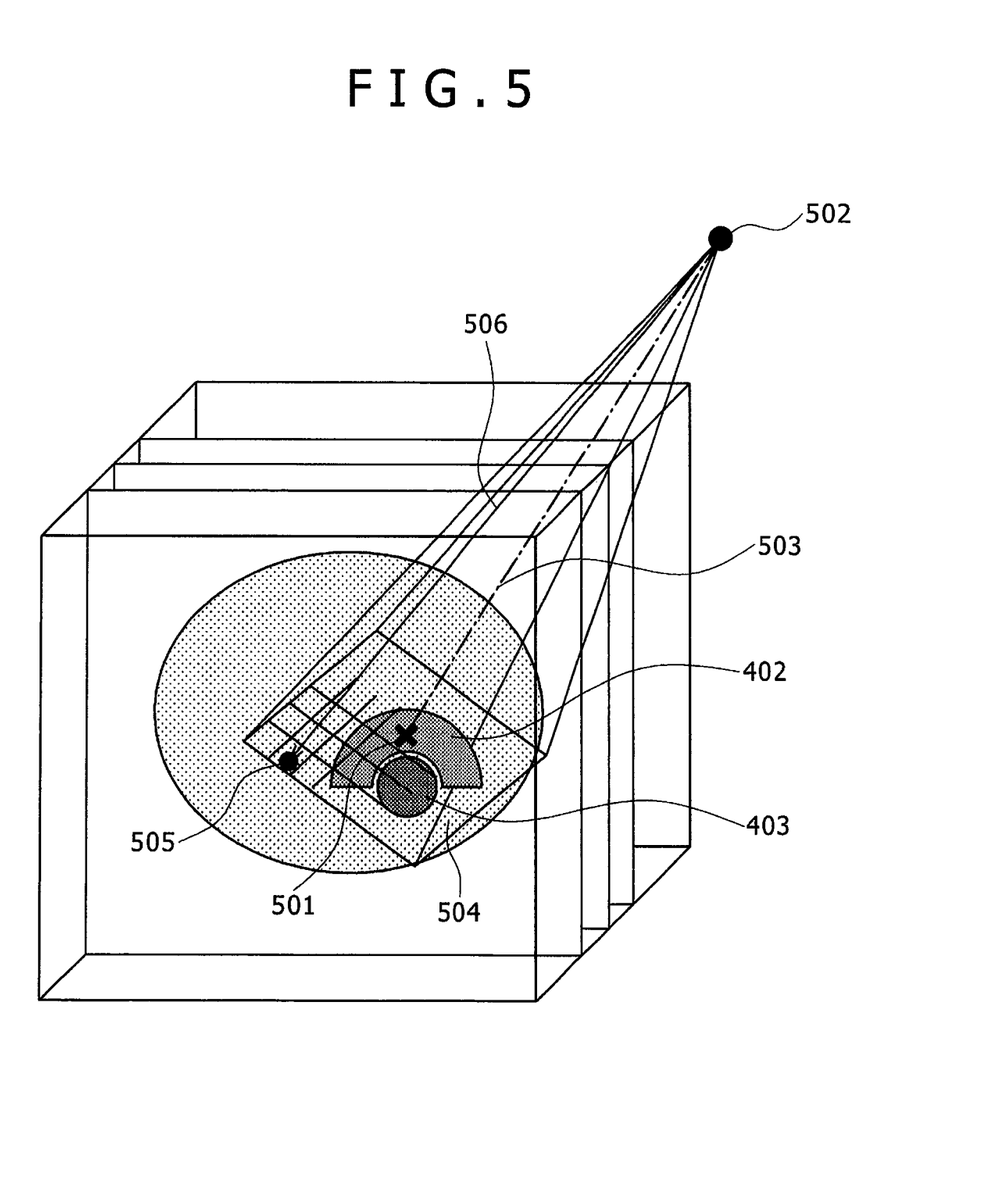
FIG. 5 is an explanatory view showing the procedure of a method for selecting spots with the embodiment.

The irradiation points selected on the isocenter plane 504 are arranged so that the spacing between adjacent irradiation points becomes less than the value designated in step 103. The simplest way of doing this may be by arraying the spots in a square matrix of which one side is designated.

Figure 7:
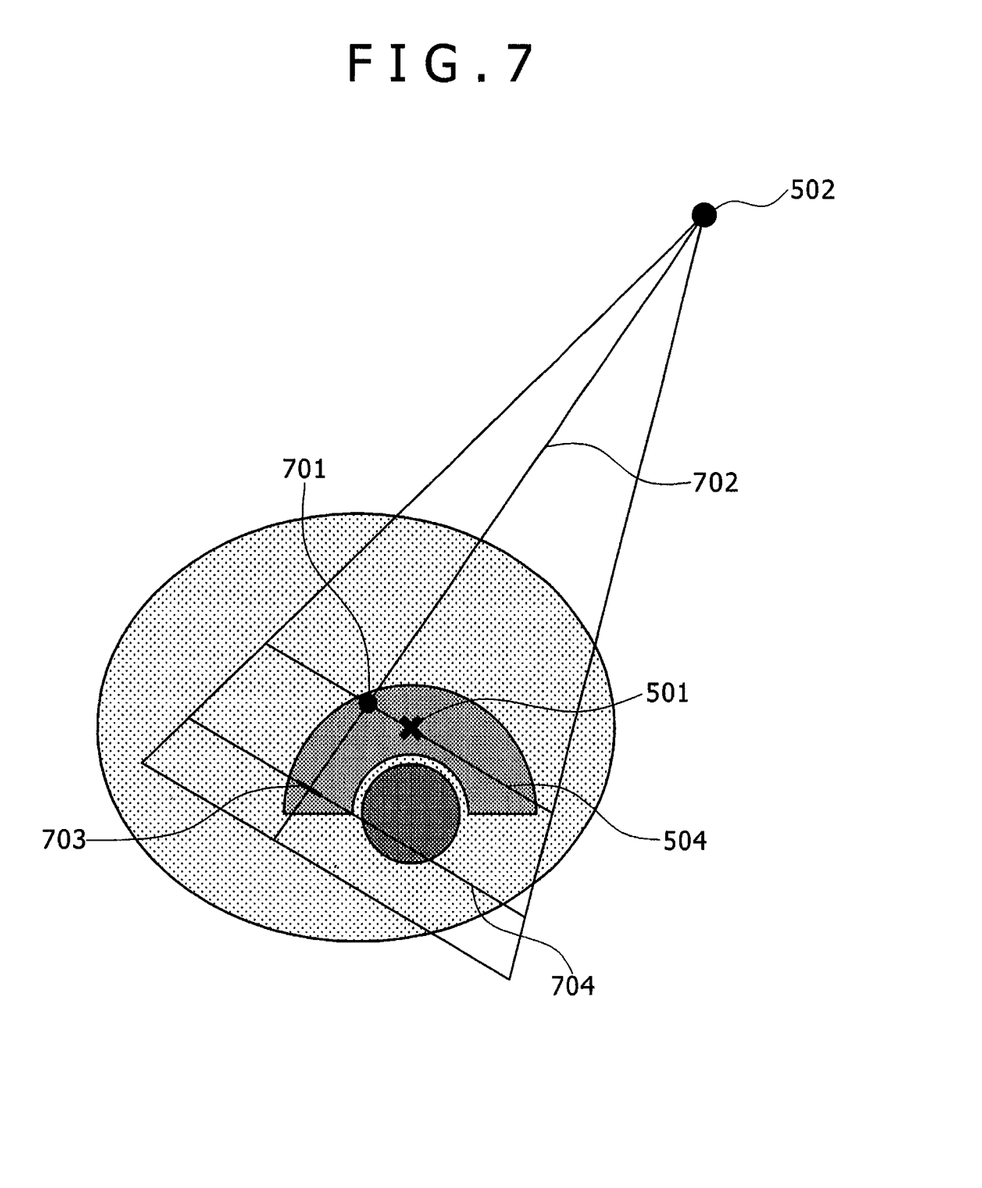
FIG. 7 is an explanatory view showing the procedure of a method for calculating the information about a particle beam stop point with the embodiment.
Figure 8:
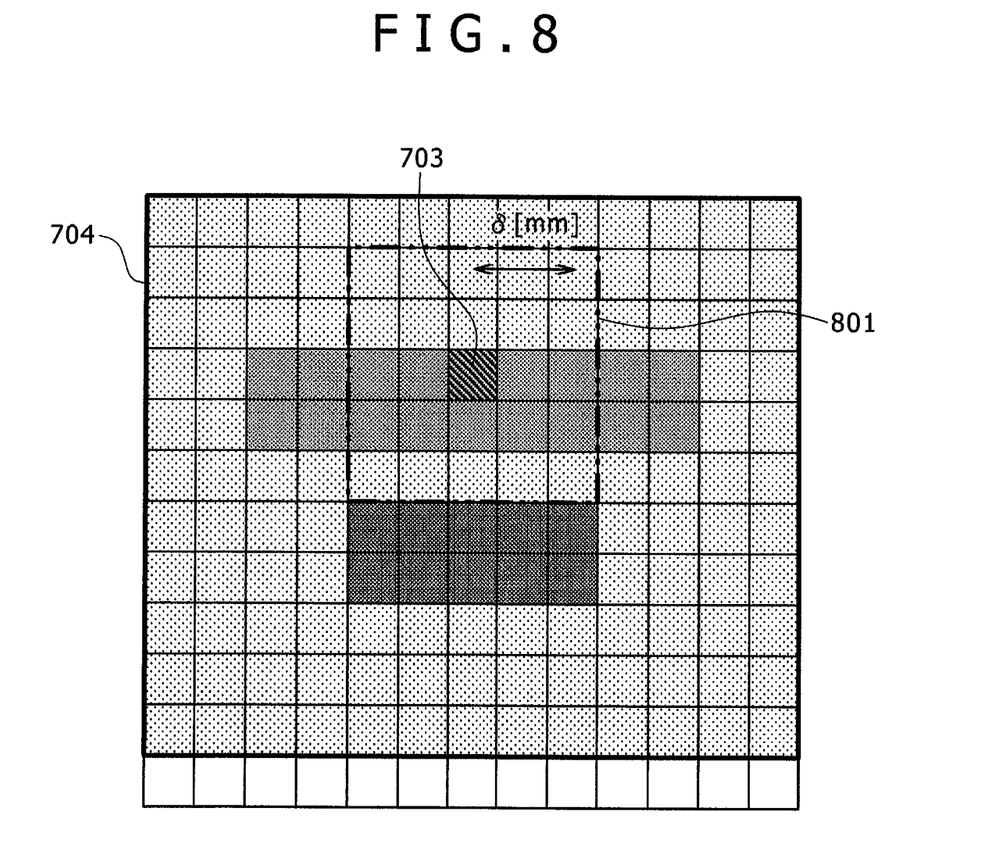
FIG. 8 is an explanatory view showing the procedure of a method for calculating a score of a setup error regarding the target region with the embodiment.

The treatment planning system 301 of this embodiment sets for each spot an index (called the score hereunder) representing the degree of demand for irradiation amount suppression (step 203). As explained above, the typical uncertainties in preparing the treatment plan include setup error and range error. The magnitude of setup error is about several millimeters or less and that of range error about several percentage points. For example, if a setup error occurs, the spots where a high-density matter such as a bone is found near the beam transmission path have their range significantly varied due to the presence of the high-density matter. This constitutes one cause of worsening the dose distribution in the target region. Thus in order to reduce the effects of setup error, the score for the spot in question needs to be set high. Also for the spots where an organ at risk is found near the beam transmission path, the score needs to be set high because a setup error or a range error that may occur can increase the dose to the organ at risk. In the description that follows, how the arithmetic processing unit 305 calculates the score is explained by referring to FIGS. 6 through 8 and by taking for example the score with regard to the setup error in the target region and the score regarding the range error on the organ at risk.

Figure 6:
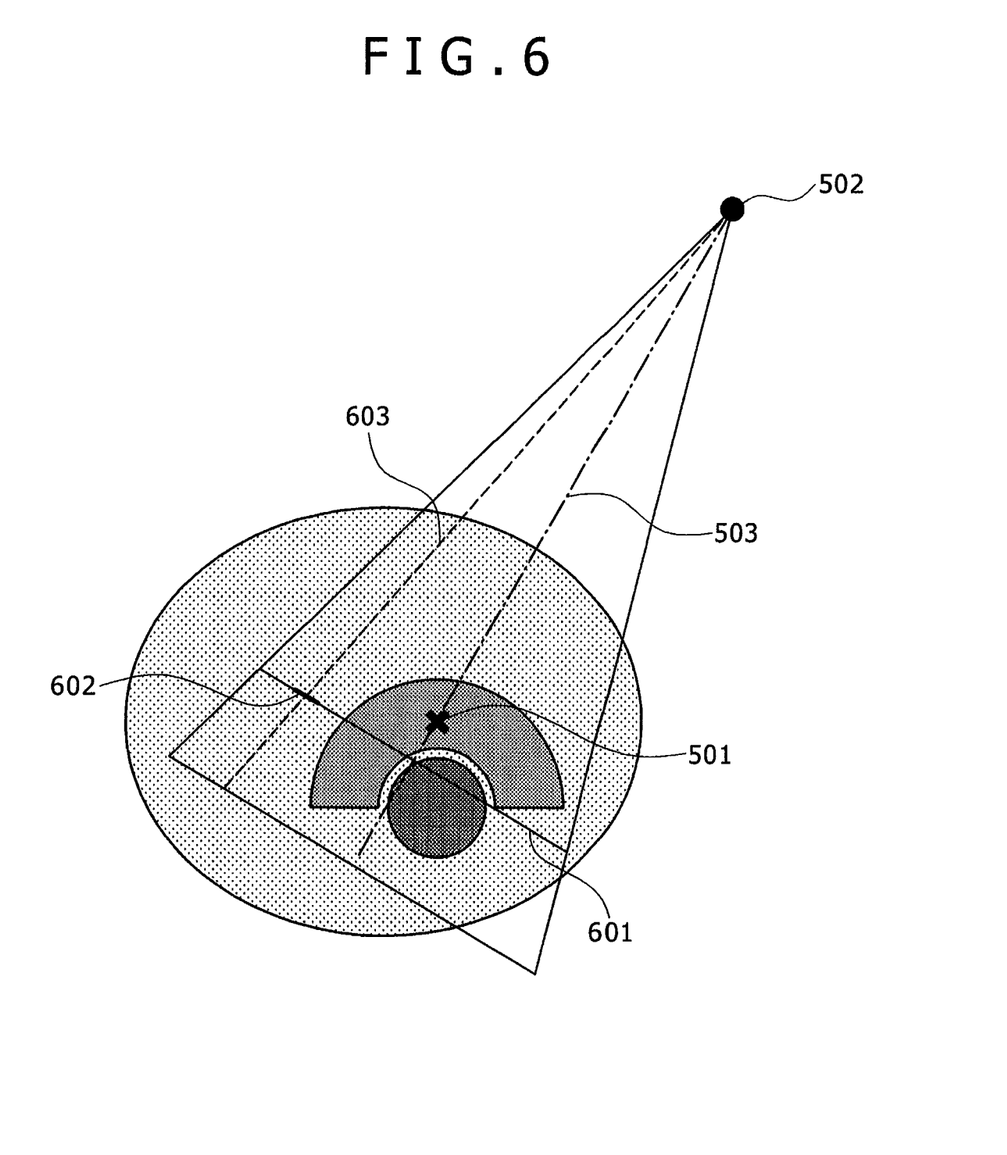
FIG. 6 is an explanatory view showing the procedure of a method for calculating a water equivalent thickness at a given position of CT data with the embodiment.

First, the arithmetic processing unit 305 of the treatment planning system 301 calculates the water equivalent thickness of a given position in the CT data. From among the irradiation condition information stored in the memory 304, the arithmetic processing unit 305 reads information indicative of the angles at which the charged particle beam is applied. The arithmetic processing unit 305 then defines a plane 601 perpendicular to the straight line 503 connecting the radiation source 502 with the isocenter 501, and divides the defined plane 601 at an appropriate resolution (usually several millimeters or less). Each of the regions thus divided is called a pixel. Then along a straight line 603 connecting the radiation source 502 with the center location of a given pixel 602, the arithmetic processing unit 305 proceeds to add up the values of CT data voxels in predetermined steps (usually at intervals of approximately the same size as the pixel 602). At this point, the CT values stored for the voxels are each added up as a thickness in effect when the material in the voxel of interest is converted to water beforehand using a table held in the memory 304 of the treatment planning system 301. The thickness is called a water equivalent thickness. The conversion from CT values to water equivalent thicknesses may be performed in one go before the calculation. The arithmetic processing unit 305 performs the calculation above on all pixels dividing the plane 601 perpendicular to the direction of beam travel. The operation above calculates the water equivalent thickness of any desired location.

The arithmetic processing unit 305 proceeds to calculate the stop position of the beam applied to each spot. The method for calculating the beam stop position is explained below with reference to FIG. 7. The arithmetic processing unit 305 first reads a spot from the memory 304. From the table held in the memory 304, the arithmetic processing unit 305 then reads the depth down to a beam stop position (i.e., position where the dose distribution peaks) with regard to the energy level of the retrieved spot. Along a straight line 702 connecting the position 701 of the retrieved spot with the radiation source 502, the arithmetic processing unit 305 references water equivalent thicknesses in predetermined steps (usually at intervals of approximately the same size as the pixel 602) to calculate the beam stop position and a pixel 703 that includes the stop position (beam stop pixel).

Using the beam stop position and the beam stop pixel 703 calculated by the above-described method, the arithmetic processing unit 305 calculates the score for each spot. How to calculate the score regarding a setup error in the target region is explained below with reference to FIGS. 7 and 8. The arithmetic processing unit 305 calculates the score on a plane 704 having the beam stop pixel 703 and perpendicular to the beam central axis. The arithmetic processing unit 305 reads a setup error δ [mm] set beforehand by the operator. Then with regard to those of pixels 801 on the plane 704 which have the distance of δ [mm] or less to the beam stop pixel 703, the arithmetic processing unit 305 calculates the sum of squares of the difference in water equivalent thickness between the beam stop pixel and each pixel and stores the result of the calculation temporarily into the memory 304 as the score of the spot. As a result, if a high-density material and a low-density material (e.g., bone, air) exist only in the vicinity of the beam transmission path, the difference in water equivalent thickness between the beam transmission path and its vicinity increases and so does the score of the spot. After calculating the scores of all spots held in the memory 304, the arithmetic processing unit 305 normalizes the scores of all spots in such a manner that the maximum score is 1, and stores the normalized scores into the memory 304.

Figure 9:
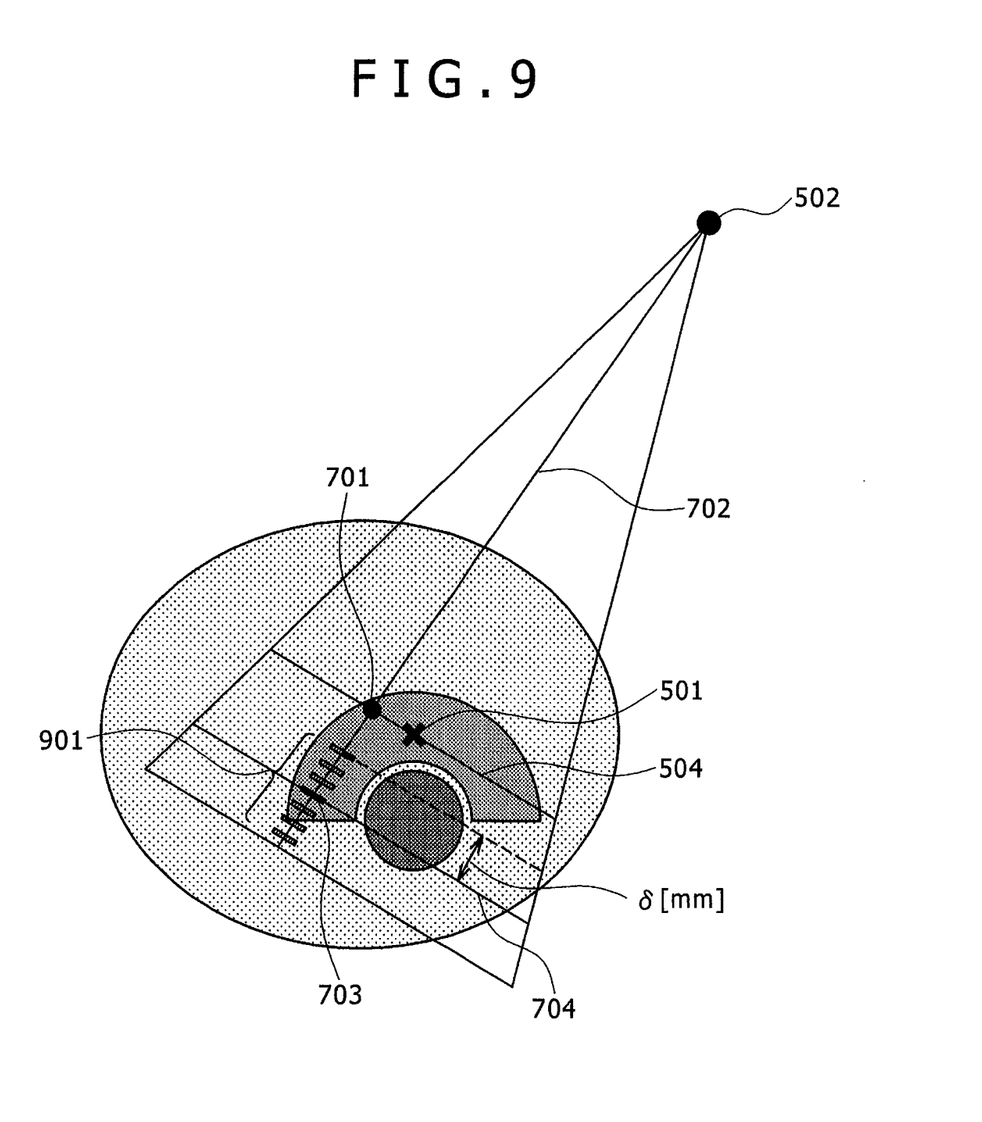
FIG. 9 is an explanatory view showing the procedure of a method for calculating a score of a range error regarding an organ at risk with the embodiment.

How to calculate the score regarding a range error on an organ at risk is explained below with reference to FIG. 9. The arithmetic processing unit 305 calculates the score along the straight line 702 connecting the radiation source 502 with the position 701 of the spot retrieved from the memory 304. First, the arithmetic processing unit 305 reads a range error δR[%] set beforehand by the operator, and obtains a calculation range δ [mm] from the water equivalent thickness of the beam stop pixel 703. Then with regard to those pixels 701 which have the distance of δ [mm] or less to the beam stop pixel 703 and which exist on the straight line 503, the arithmetic processing unit 305 determines whether each pixel is found within the organ at risk registered in step 102. The arithmetic processing unit 305 stores the total number of the pixels found in the organ at risk temporarily into the memory as the score of the spot. As a result, the value of the score is larger, the closer the beam stop spot is to the organ at risk. After calculating the scores of all spots held in the memory 304, the arithmetic processing unit 305 normalizes the scores of all spots in such a manner that the maximum score is 1 and stores the normalized scores into the memory 304.

Figure 10:
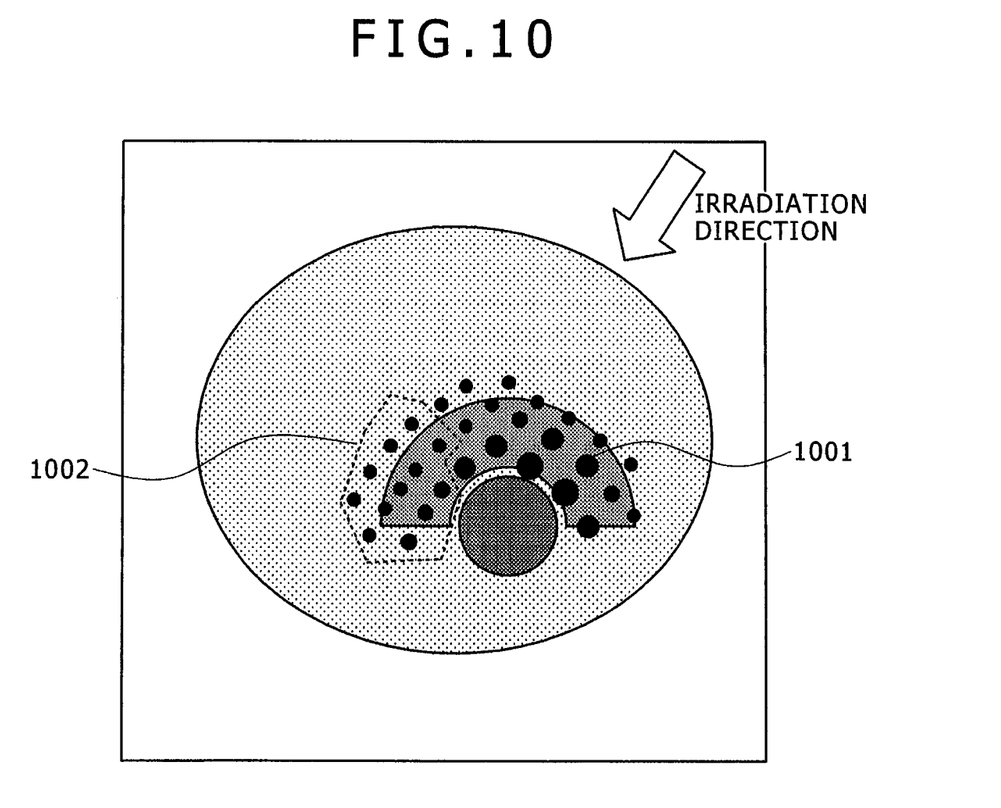
FIG. 10 is a schematic view showing beam stop points overlaid on a patient's CT data displayed on a display unit, where the size of each of the points in the drawing indicates the magnitude of the score set for each spot.

The scores of the spots calculated in the manner described above can be visually verified. The display unit 303 displays the irradiation points corresponding to the energy levels of the irradiation spots. It is also possible to overlay the beam stop positions of the beam applied to the spots onto the patient's computed tomography slice image. FIG. 10 shows an example in which beam stop positions are displayed overlaid on a slice 401 of the CT data in FIG. 4. Points 1001 each indicate the location where the beam applied to the spot is stopped. The score set for each spot may also be displayed using the size or color of the point. In FIG. 10, the magnitude of the score is indicated by the size of each point.

It is also possible for the operator using the input unit 302 to prepare a desired region 1002 on the display screen of the display unit 303 and change the scores of the spots in the region thus prepared. For example, if it has been determined by experience that a metal artifact has occurred in the CT data and that there are high uncertainties in the region where the metal artifact has been formed, the operator using the input unit 302 prepares the region with its scores set to cover the artifact-forming region. For each spot where the beam stops within that region, the operator sets a desired value as a score. By designating in this manner the region for which to set scores, the operator can set the scores for a plurality of spots in one go.

After the scores are set for all the spots that have been set, the arithmetic processing unit 305 of the treatment planning system 301 performs optimized calculation of the irradiation amount under the operator's operating directions. Usually, the treatment planning system 301 defines an objective function in which the divergence between the irradiation amount and the prescription dose is quantified (step 204). The treatment planning system 301 calculates the irradiation amount as a parameter of the objective function in a manner minimizing the divergence through iterative calculation (step 205). The treatment planning system 301 of this embodiment takes into account the score set for each spot in the objective function, thereby suppressing the irradiation amount to specific spots so as to reduce the effects of uncertainties on the treatment plan being prepared. The arithmetic processing unit 305 generates (defines) the objective function as follows:

The arithmetic processing unit 305 sets "n1" points and "n" points at which to calculate the dose in the target region 401 and in the organ at risk 402, respectively. The dose at each of these points should satisfy as much as possible the prescription dose input by the operator in step 103. It is assumed here that a target dose "p" is set for the "m" points corresponding to the target region 401 and a permissible dose "l" is set for the "n" points corresponding to the organ at risk 402. The vector of which the elements are the spot irradiation amounts constituting parameters of the objective function is expressed as $$\vec{x}$$

of which the dimension is the total number "k" of spots. Next, if the vector of which the elements are the doses for the "m" points in the target region 401 is express as $\vec{d}^{(1)}$ then the relationship to the irradiation amount for each spot is expressed using the following expression (1):

$$\vec{d}^{(1)} = A\vec{x} \quad (1)$$

The matrix A represents a contribution of the beam applied to each spot to the points inside the target region. The arithmetic processing unit 305 in the treatment planning system calculates the matrix A based on the directions of irradiation and on the body information in computed tomography images, both information being held in the memory 304.

Likewise, if the vector of which the elements are the doses for the "n" points in the organ at risk 402 is expressed as $\vec{d}^{(2)}$ then the relationship to the irradiation amount $\vec{x}$ for each spot is expressed using the following expression (2):

$$\vec{d}^{(2)} = B\vec{x} \quad (2)$$

After calculating the matrices A and B, the arithmetic processing unit 305 uses the vector denoting the score set for each spot in step 203 to generate the following objective function:

$$F(\vec{x}) = \sum_{i=1}^{m} w_i^{(1)}(d_i^{(1)} - p)^2 + \sum_{i=1}^{n} w_i^{(2)}(d_i^{(2)} - l)^2 \theta(d_i^{(2)} - l) + K_0 \sum_{j=1}^{k} S_j x_j,$$

In the expression (3) above, the first member "$w_i^{(1)}$" and the second member "$w_i^{(2)}$" on the right side are the weights corresponding to the respective points and are input by the operator in step 103 along with the prescription dose. The first and the second members on the right side of the expression (3) also apply to related-art treatment planning systems and are members that control the dose distribution in a manner meeting the prescription dose. The first member on the right side of, the expression (3) is a part that controls the dose in the target. The closer the dose to the "m" points is to the prescription dose "p" set as the target, the smaller the value $F(\vec{x})$ The second member on the right side of the expression (3) is a member that controls the dose in the organ at risk. The dose to the organ at risk is acceptable as long as it does not exceed the permissible dose "l." $\theta(d_i^{(2)}-l)$ in the second member on the right side of the expression (3) represents a step function that is 0 when $d_i^{(2)}<1$ and is 1 otherwise.

The third member on the right side of the expression (3) is a member which directly controls the irradiation amount to each spot and which characterizes this embodiment. The lower the ratio of the irradiation amount to spots having large scores $S_j$, the smaller the value $F(\vec{x})$ so that the third member is controlled to lower the irradiation amount to the spots having larger scores $S_j$ and raise the irradiation amount to the spots having smaller scores $S_j$. When the scores are set high for the spots that will cause the dose distribution to be significantly affected by the uncertainties in preparing the treatment plan, it is possible to search for the irradiation amount $\vec{x}$ that can reduce the effects of the uncertainties on the dose distribution.

Also, $K_0$ denotes the degree of importance of the third member. Although the initial value of $K_0$ is automatically set, it may be changed by the operator. Based on the value of $K_0$, it is possible to select one of two solutions: one in which the control of the dose distribution (using the first and the second members of the expression (3)) is given priority, and the other in which the control of the irradiation amount to spots (using the third member of the expression (3)) is given priority. If the operator sets 0 in $K_0$, the third member of the expression (3) is ignored.

After generating the objective function of the expression (3) above, the arithmetic processing unit 305 performs iterative calculation to search for $\vec{x}$ that will minimize $F(\vec{x})$ Non-Patent Literature 1 cited above gives detailed examples of iterative calculation.

When optimized calculation is performed with the amount of change in density near the beam transmission path set as scores, the irradiation amount to the spots where the density change is pronounced can be reduced. Thus if a setup error has occurred, it is possible to suppress the irradiation amount to the spots where the amount of density change on the beam transmission path alters the range appreciably and thereby to minimize the worsening of the dose distribution over the target region.

Meanwhile, if optimized calculation is performed with the degree of presence of an organ at risk on the beam transmission path set as a score in case of a range error, it is possible to suppress the irradiation amount to the spots that are prone to convey the dose to the organ at risk in the event of a range error. This in turn makes it possible to suppress range error-triggered excessive irradiation to the organ at risk.

Once the irradiation amounts are determined through iterative calculation, the treatment planning system 301 calculates the dose distribution using the ultimately obtained spot locations and the irradiation amount to each of the spots. The results of the calculations are displayed on the display unit 303 (steps 206 and 207). The operator verifies on the display unit 303 whether the designated doses are applied to the target region in just proportion (step 106).

For verification of the dose distribution over the target region, a histogram called DVH (Dose Volume Histogram) is also used extensively. The treatment planning system 301 uses the arithmetic processing unit 305 to calculate the values of DVH before having them displayed on the display unit 303.

The operator analyzes the resulting dose distribution using the dose distribution and DVH which are displayed on the displayed unit 303 so as to determine whether the dose distribution meets the targeted conditions (step 107). If the distribution is not what is desired, step 103 is reached again and the irradiation conditions are again set. The irradiation conditions to be changed include the direction of irradiation and the spot-to-spot spacing. After the conditions have been changed, the treatment planning system 301 calculates the spots and irradiation amounts under the operator's instructions and causes the display unit 303 to display the newly obtained dose distribution. When the desired results are obtained, the preparation of the treatment plan is terminated (steps 108 and 109). The irradiation conditions thus obtained are stored into the data server 307 via the network.

There are two types of scanning irradiation: spot scanning method and raster method. According to the spot scanning method, after the beam of a predetermined dose is applied to an irradiation point, the beam is stopped temporarily while the next irradiation point is being reached for irradiation. When the next irradiation point is reached, the irradiation of the beam is resumed. The raster method involves allowing the irradiation of the beam to continue after the irradiation of one point is completed and while the next irradiation point is being reached. The above-described embodiment has presupposed the use of the spot scanning method. Where the raster method is in use, obtaining the irradiation conditions requires setting a plurality of irradiation points in order to perform discrete calculations. The radiation treatment planning system of the present invention can also be used to prepare treatment plans in conjunction with the raster method.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A radiation treatment planning system for preparing treatment planning information for carrying out radiation treatment, the radiation treatment planning system comprising:
an input unit with which an operator inputs a prescription dose and an irradiation angle;
an arithmetic unit which prepares the treatment planning information by determining irradiation conditions in such a manner as to bring a dose distribution calculated based on the inputs from the input unit closer to the prescription dose; and
a display unit which displays the treatment planning information,
wherein the arithmetic unit sets, per radiation irradiation point of the radiation treatment, an index representing a degree of demand for irradiation amount suppression, the degree of demand determined by the radiation irradiation point, and the arithmetic unit further determines the irradiation conditions using the index according to the following expression:

$$F(\vec{x}) = \sum_{i=1}^{m} w_i^{(1)}(d_i^{(1)} - p)^2 + \sum_{i=1}^{n} w_i^{(2)}(d_i^{(2)} - l)^2 \theta(d_i^{(2)} - l) + K_0 \sum_{j=1}^{k} S_j x_j,$$

where "p" is a target dose set for "m" points corresponding to a target region, "$w_i^{(1)}$" are weights corresponding to the "m" points, and "$\vec{d}^{(1)}$" are doses for the "m" points in the target region,
where "l" is a permissible dose set for "n" points corresponding to an organ at risk, "$w_i^{(2)}$" are weights corresponding to the "n" points, "$\vec{d}^{(2)}$" are doses for the "n" points in the organ at risk, and "$\theta(d_i^{(2)}-l)$" is a step function that is 0 when $d_i^{(2)} < l$ and is 1 otherwise, and
where "$K_0$" is a degree of importance greater than 0, "$S_j$" are scores representing a degree of demand for irradiation amount suppression, and "$\vec{x}$" are irradiation amounts for a total number "k" of spots.

2. The radiation treatment planning system according to claim 1, wherein the arithmetic unit determines the index in accordance with density information for a patient, the density information being based on the result of the inputs from the input unit.

3. The radiation treatment planning system according to claim 2, wherein the arithmetic unit sets the index with regard to the radiation irradiation points included in a desired region designated using the input unit.

4. The radiation treatment planning system according to claim 1, wherein the arithmetic unit causes information about the set index to be displayed on the display unit.

5. The radiation treatment planning system according to claim 4, wherein the arithmetic unit sets the index with regard to the radiation irradiation points included in a desired region designated using the input unit.

6. The radiation treatment planning system according to claim 1, wherein the arithmetic unit sets the index with regard to the radiation irradiation points included in a desired region designated using the input unit.

* * * * *